US00PP17574P2

(12) United States Plant Patent
Hambali

(10) Patent No.: US PP17,574 P2
(45) Date of Patent: Apr. 3, 2007

(54) *CALATHEA* PLANT NAMED 'TWYCA0018'

(50) Latin Name: *Calathea hybrida*
Varietal Denomination: TWYCA0018

(75) Inventor: Gregori G. Hambali, Bogor (ID)

(73) Assignee: Twyford International, Inc., Apopka, FL (US)

( * ) Notice: Subject to any disclaimer, the term of this patent is extended or adjusted under 35 U.S.C. 154(b) by 0 days.

(21) Appl. No.: 11/245,378

(22) Filed: Oct. 6, 2005

(51) Int. Cl.
*A01H 5/00* (2006.01)

(52) U.S. Cl. ..... Plt./375

(58) Field of Classification Search ..... Plt./375
See application file for complete search history.

*Primary Examiner*—Kent Bell
(74) *Attorney, Agent, or Firm*—C. A. Whealy

(57) ABSTRACT

A new and distinct cultivar of *Calathea* plant named 'TWYCA0018', characterized by its upright and outwardly spreading growth habit; freely basally branching habit; and elliptic-shaped leaves with alternating dark and light green-colored chevrons and double-ringed dark green-colored margins.

2 Drawing Sheets

Botanical designation: *Calathea hybrida.*
Cultivar denomination: 'TWYCA0018'.

BACKGROUND OF THE INVENTION

The present Invention relates to a new and distinct cultivar of *Calathea* plant, botanically known as *Calathea hybrida,* and hereinafter referred to by the name 'TWYCA0018'.

The new *Calathea* is a product of a planned breeding program conducted by the Inventor in Bogor, Indonesia. The objective of the breeding program is to create new fast-growing *Calathea* cultivars with freely branching habit and attractive leaf coloration.

The new *Calathea* originated from a cross-pollination made by the Inventor in Bogor, Indonesia in February, 1999, of an unnamed selection of *Calathea loesenerii*×*Calathea illustris,* not patented, as the female, or seed, parent with an unnamed selection of *Calathea libbyana,* not patented, as the male, or pollen, parent. The cultivar of TWYCA0018 was discovered and selected by the Inventor as a single plant within the progeny of the stated cross-pollination in a controlled environment in Bogor, Indonesia in October, 2001.

Asexual reproduction of the new *Calathea* by divisions in a controlled environment in Bogor, Indonesia has shown that the unique features of this new *Calathea* are stable and are reproduced true to type in successive generations.

SUMMARY OF THE INVENTION

Plants of the cultivar TWYCA0018 have not been observed under all possible environmental conditions. The phenotype may vary somewhat with variations in environment such as temperature and/or light intensity without, however, any variance in genotype.

The following traits have been repeatedly observed and are determined to be the unique characteristics of 'TWYCA0018'. These characteristics in combination distinguish 'TWYCA0018' as a new and distinct cultivar:

1. Upright and outwardly spreading growth habit.
2. Freely basally branching habit.
3. Elliptic-shaped leaves with alternating dark and light green-colored chevrons and double-ringed dark green-colored margins.

Plants of the new *Calathea* can be compared to the female parent selection. However, plants of the new *Calathea* differ from plants of the female parent selection primarily in leaf coloration as plants of the female parent selection only have a single dark green-colored ring around the margin.

Plants of the new *Calathea* can be compared to plants of the male parent selection. However, plants of the new *Calathea* differ from plants of the male parent selection in the following characteristics:

1. Plants of the new *Calathea* are more freely basal branching than plants of the male parent selection.
2. Plants of the new *Calathea* and the male parent selection differ in leaf coloration as plants of the male parent selection only have a single dark green-colored ring around the margin.

Plants of the new *Calathea* can also be compared to plants of the *Calathea libbyana* cultivar Window, not patented. In side-by-side comparisons conducted in Apopka, Fla., plants of the new *Calathea* differed from plants of the cultivar Window in the following characteristics:

1. Plants of the new *Calathea* are more freely basal branching than plants of the cultivar Window.
2. Plants of the new *Calathea* and the cultivar Window differ in leaf coloration as plants of the cultivar Window only have a single dark green-colored ring around the margin.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new *Calathea.*

The photograph on the first sheet comprises a top perspective view of a typical flowering plant of 'TWYCA0018' grown in a container.

The photographs on the second sheet comprise close-up views of the upper and lower surfaces of developing leaves (top of sheet) and upper and lower surfaces of fully developed leaves (bottom of sheet) of 'TWYCA0018'.

DETAILED BOTANICAL DESCRIPTION

Plants used for the aforementioned photographs and the following description were grown for about one year in 10-cm containers in Apopka, Fla., in a polyethylene-covered greenhouse with day temperatures ranging from 27° C. to 29° C., night temperatures about 20° C. and light levels ranging from 1,500 to 2,500 foot-candles.

All color references are measured against The Royal Horticultural Society Colour Chart, 2001 Edition. Colors and numerical measurements are approximate as plant growth and development depends on environmental conditions and cultural practices such as light level and temperature, among others, without, however any variance in genotype.

Botanical classification: *Calathea hybrida* cultivar TWYCA0018.

Parentage:

*Female, or seed, parent.*—Unnamed selection of *Calathea loesenerri*×*Calathea illustris,* not patented.

*Male, or pollen, parent.*—Unnamed selection of *Calathea libbyana,* not patented.

Propagation:

*Type.*—By tissue culture.

*Time to initiate roots on tissue-cultured plants.*—Summer: About two weeks at temperatures of 26° C. Winter: About three weeks at temperatures of 21° C.

*Time to produce a rooted tissue-cultured plant.*—Summer: About ten weeks at 26° C. Winter: About twelve weeks at 21° C.

*Root description.*—Main roots, tough, wiry, fibrous; lateral roots, fine; dark brown in color.

Plant description:

*Form.*—Upright and broad outwardly spreading growth habit; freely clumping; leaves emerging from the base in a rosette; about five to six basal branches per plant.

*Plant height.*—About 25.75 cm.

*Plant width.*—About 42.4 cm.

*Rhizome description.*—Length: About 3 cm. Diameter: About 1.3 cm. Texture: Smooth, glabrous. Color: 179C to 179D.

*Foliage description.*—Arrangement: Alternate, simple. Length: About 19.1 cm. Width: About 10.5 cm. Shape: Elliptic. Apex: Acuminate. Base: Obtuse. Margin: Entire; undulate. Texture, upper and lower surfaces: Smooth, glabrous; rugose. Venation pattern: Pinnate. Color: Developing foliage, upper surface: Towards the margin, 147B to 147C; four alternating light and dark-colored outer rings adjacent to margin, 146D, 147A to 147B, 145B to 145C, and 147A to 147B; alternating light and dark-colored chevrons, 145C to 145D and 147A; along midvein, 144A; midvein, 145C; lateral venation, 137B or similar to lamina coloration.

Developing foliage, lower surface: Towards the margin, 187A to 187B; four alternating light and dark-colored outer rings adjacent to margin, 191A, 187A to 187B, 145B, and 187A and 187B; alternating light and dark-colored chevrons, darker green than 138C and 187A to 187B; midvein, 147C tinged with 193A; lateral venation, 137A, N186C or similar to lamina coloration. Fully expanded foliage, upper surface: Towards the margin, 147A; four alternating light and dark-colored outer rings adjacent to margin, more green than 147B, 147A, 145C, and 147A to 147B; alternating light and dark-colored chevrons, slightly darker than 145A and 147A; along midvein, more green than 144A; midvein, 144B; lateral venation, 137B or similar to lamina coloration. Fully expanded foliage, lower surface: Towards the margin, 187A; four alternating light and dark-colored outer rings adjacent to margin, 191A, N186C, 145B to 138B, and N186C; alternating light and dark-colored chevrons, 148C to 148D tinged with 191A, and N186A; midvein, 147C tinged with N186C; lateral venation, 137A, 191A or similar to lamina coloration.

*Petiole description.*—Length: About 18.5 cm. Diameter: About 3 mm. Texture, upper and lower surfaces: Fine pubescence. Color, upper surface: 146A. Color, lower surface: 146B. Leaf sheath: Length: About 11.5 cm. Width: About 8 mm. Apex: Tapering and becoming flush with the petiole. Texture, upper and lower surfaces: Fleshy. Color, outside: 166A tinged with 186C. Color, inside: Towards the center, 191B to 191C; towards the margin, 181B. Geniculum: Length: About 2.4 cm. Width: About 4 mm. Texture, upper and lower surfaces: Fine pubescence. Color, upper and lower surfaces: 146D.

Inflorescence description: Inflorescence development has not been observed on plants of the new *Calathea.*

Disease/pest resistance: Under commercial production conditions, plants of the new *Calathea* have not been noted to be resistant to pathogens or pests common to *Calathea.*

Temperature tolerance: Plants of the new *Calathea* have been observed to tolerate temperatures from 4° C. to 32° C. in Apopka, Fla.

It is claimed:

1. A new and distinct cultivar of *Calathea* plant named 'TWYCA0018', as illustrated and described.

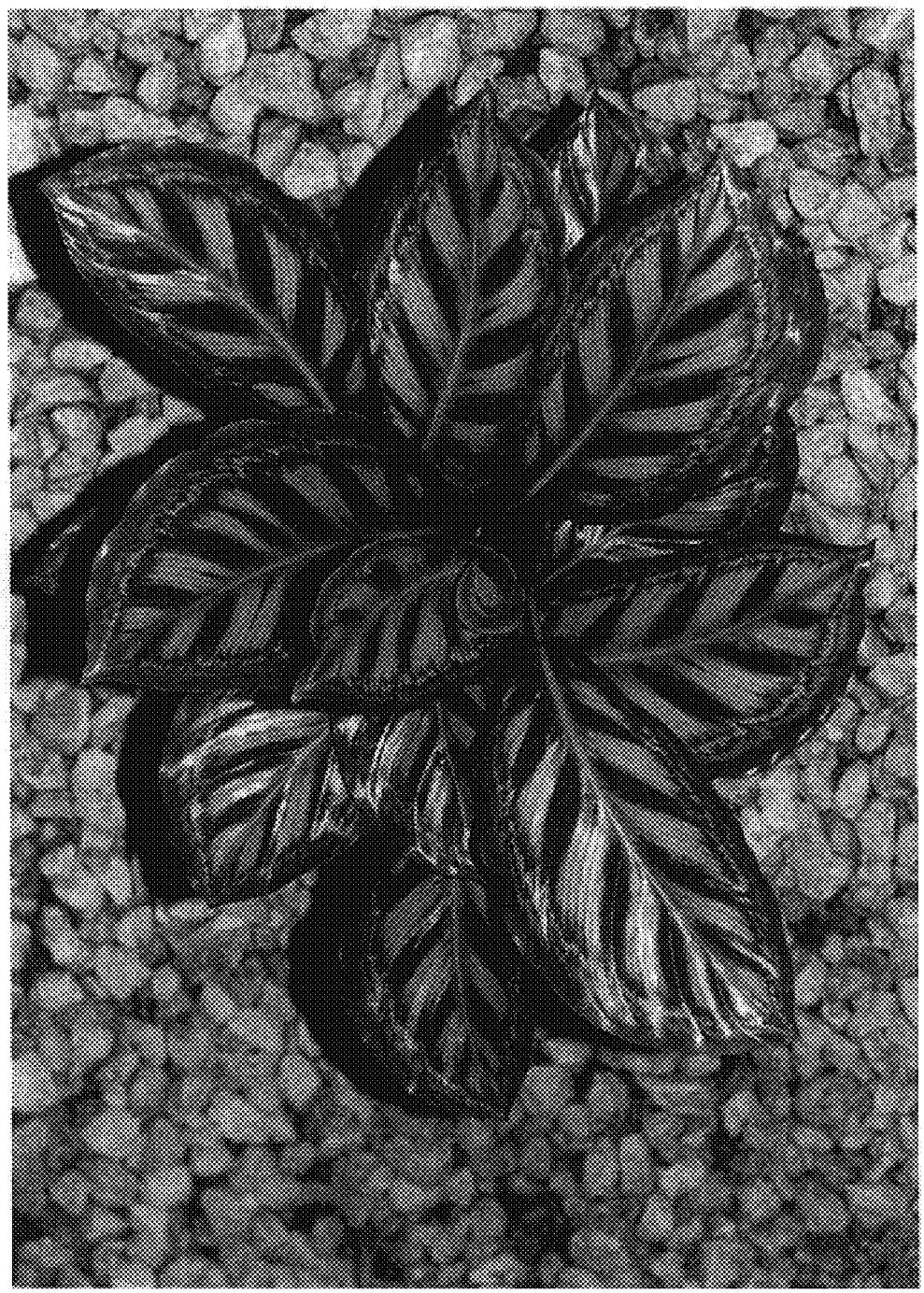

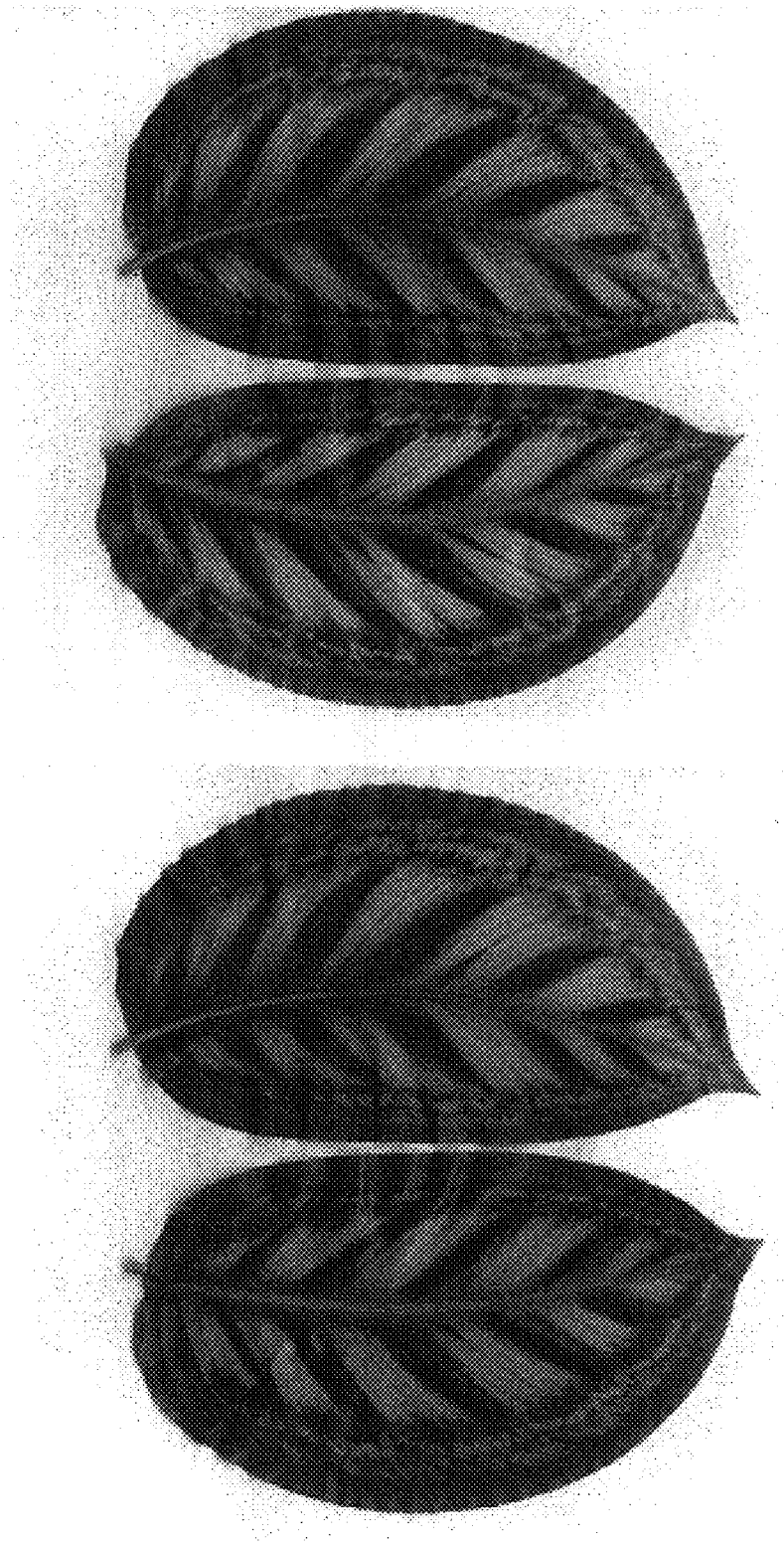

* * * * *